(12) United States Patent
Fujii et al.

(10) Patent No.: US 7,838,855 B2
(45) Date of Patent: Nov. 23, 2010

(54) CHARGED PARTICLE IRRADIATION SYSTEM

(75) Inventors: Yusuke Fujii, Hitachi (JP); Hisataka Fujimaki, Nissin (JP); Kazuo Hiramoto, Hitachiohta (JP)

(73) Assignee: Hitachi, Ltd., Tokyo (JP)

( * ) Notice: Subject to any disclaimer, the term of this patent is extended or adjusted under 35 U.S.C. 154(b) by 335 days.

(21) Appl. No.: 12/141,603

(22) Filed: Jun. 18, 2008

(65) Prior Publication Data

US 2009/0039256 A1    Feb. 12, 2009

(30) Foreign Application Priority Data

Jun. 22, 2007  (JP) .............................. 2007-164990

(51) Int. Cl.
*A61N 5/00* (2006.01)
*H05H 13/04* (2006.01)
*G21K 5/10* (2006.01)

(52) U.S. Cl. ............... 250/505.1; 250/491.1; 250/493.1; 250/492.3; 315/503; 315/507; 315/111.61; 378/65

(58) Field of Classification Search ............... 250/505.1, 250/491.1, 493.1, 492.3; 315/503, 507, 111.81; 378/65
See application file for complete search history.

(56) References Cited

U.S. PATENT DOCUMENTS

| 6,677,597 | B1 | 1/2004 | Haberer et al. | |
|---|---|---|---|---|
| 6,736,831 | B1 | 5/2004 | Hartmann et al. | |
| 6,774,383 | B2 * | 8/2004 | Norimine et al. | 250/505.1 |
| 6,936,832 | B2 | 8/2005 | Norimine et al. | |
| 7,060,997 | B2 | 6/2006 | Norimine et al. | |
| 7,301,162 | B2 * | 11/2007 | Matsuda et al. | 250/505.1 |
| 7,439,528 | B2 * | 10/2008 | Nishiuchi et al. | 250/492.3 |
| 2003/0183779 | A1 | 10/2003 | Norimine et al. | |
| 2005/0082498 | A1 | 4/2005 | White | |
| 2006/0033042 | A1 | 2/2006 | Groezinger et al. | |

FOREIGN PATENT DOCUMENTS

| EP | 1 348 465 | 10/2003 |
|---|---|---|
| EP | 1 621 228 | 2/2006 |
| EP | 1 656 966 | 5/2006 |
| EP | 1 936 655 | 6/2008 |
| JP | 2002-540911 | 12/2002 |
| JP | 2003-282300 | 10/2003 |
| JP | 2005-296162 A | 10/2005 |
| JP | 2005-329252 | 12/2005 |
| JP | 2007-132902 A | 5/2007 |

* cited by examiner

*Primary Examiner*—Nikita Wells
(74) *Attorney, Agent, or Firm*—Mattingly & Malur, P.C.

(57) ABSTRACT

A charged particle irradiation system that positions the beam at a target position to avoid irradiation of normal tissue includes an acceleration system 6 for extracting a charged particle beam, scanning magnets 24 and 25, and charged particle beam position monitors 26 and 27. On the basis of signals received from the charged particle beam position monitors 26 and 27, the control unit 70 calculates a beam position at a target position and then controls the scanning magnets 24 and 25 so that the charged particle beam is moved to a desired irradiation position at the target position. The control unit 70 corrects the value of an excitation current applied to each of the scanning magnets 24 and 25 on a specified cycle basis on the basis of information about the position and the angle of the charged particle beam.

19 Claims, 6 Drawing Sheets

CHARGED PARTICLE IRRADIATION SYSTEM

BACKGROUND OF THE INVENTION

1. Field of the Invention

The present invention relates to a charged particle irradiation system that is used to irradiate an affected part such as a tumor with a charged particle beam so as to treat the affected part and more particularly to a charged particle irradiation system that is suitable for the correction of a beam position.

2. Description of the Related Art

There is known a charged particle irradiation system for irradiating a patient such as a cancer patient with a charged particle beam such as a proton beam. This charged particle irradiation system includes an ion beam generator, a beam transport line, and a treatment room. A charged particle beam accelerated by the ion beam generator reaches an irradiation nozzle in the treatment room through the beam transport line. The charged particle beam is then scanned by a scanning magnet included in the irradiation nozzle so that an affected part of the patient is irradiated with the charged particle beam. Heretofore, as a method used in such a charged particle irradiation system, there is known an irradiation method including the steps of: with irradiation with a charged particle beam from the ion beam generator stopped, controlling the scanning magnet so that the irradiation position of the charged particle beam is changed; and then restarting the irradiation.

Such an irradiation method is required to achieve a high degree of accuracy in position and angle of a charged particle beam. However, the position and angle of the charged particle beam from the ion beam generator may not be stable. As a solution to this, there is known a technology in which two steering magnets are disposed in a beam transport line so as to correct the trajectory of a charged particle beam (for example, refer to JP-A-2003-282300).

Moreover, there is known a technology in which beam position information acquired by a charged-particle-beam-position monitor system is used to control a scanning magnet so that a beam position is corrected (for example, refer to Published Japanese translation of PCT application No. 2002-540911).

SUMMARY OF THE INVENTION

However, according to the technology described in JP-A-2003-282300, other magnets exist between the steering magnet and an irradiation nozzle. Therefore, in order to correctly correct the position and angle, it is necessary to perform the convergence a plurality of times. Thus, the problem with the above technology is that it is difficult to correctly make an instantaneous correction.

Moreover, according to the technology described in PCT application No. 2002-540911, if the position of a charged particle beam which is measured at the position of a charged-particle-beam-position monitor system deviates from a desired position, the scanning magnet is controlled to move the charged particle beam to the desired position. However, because both of the position and angle of the charged particle beam change, even if a charged particle beam position at the position of the charged-particle-beam-position monitor system is correct, there is a possibility that the charged particle beam will not reach the desired position at a target position further downstream of the charged particle beam in comparison with the charged-particle-beam-position monitor system.

An object of the present invention is to provide a charged particle irradiation system that is capable of improving the accuracy in irradiation position of a charged particle beam at a target position and is capable of decreasing the possibility that a normal tissue will be irradiated.

(1) In order to achieve the above-mentioned object, according to one aspect of the present invention, there is provided a charged particle irradiation system comprising:

an accelerator for extracting a charged particle beam;

charged-particle-beam scanning equipment; and a charged-particle-beam-position monitor system, wherein said charged particle irradiation system further includes a control unit for calculating a beam position at a target position on the basis of a signal received from the charged-particle-beam-position monitor system to control the charged-particle-beam scanning equipment so that the charged particle beam is moved to a desired irradiation position at the target position.

Because a beam position at a target position is calculated by the above-described configuration, it is possible to improve the accuracy in irradiation position of a charged particle beam at the target position and thereby to decrease the possibility that a normal tissue will be irradiated.

(2) In the above-described item (1), said control unit preferably corrects the value of an excitation current applied to the charged-particle-beam scanning equipment on a specified cycle basis on the basis of information about the position and the angle of the charged particle beam.

(3) In the above-described item (1), in each extraction cycle of the accelerator, said control unit preferably corrects the value of an excitation current applied to the charged-particle-beam scanning equipment on the basis of information about the position and the angle of the charged particle beam.

(4) In the above item (1), said control unit preferably sets an excitation current value for the charged-particle-beam scanning equipment such that in the next cycle, a point on the opposite side of the charged particle beam position with respect to the desired irradiation position, which point is away from the beam position by the distance between the beam position and the desired position at the target position, is irradiated with such a charged particle beam with which the beam position agrees with the desired irradiation position.

(5) In the above-described item (3), even when the charged-particle-beam scanning equipment scans the charged particle beam, said control unit preferably calculates the distance between the desired position and the charged particle beam position at the target position on the basis of the distance between the position of the charged particle beam traveling toward the desired irradiation position at the position of the charged-particle-beam-position monitor system and the path of the charged particle beam.

(6) In the above-described item (1), said control unit preferably identifies the progress of the phase of the extraction cycle from a radiated charge amount in the same extraction cycle.

(7) In the above-described item (1), said control unit preferably identifies the progress of the phase of the extraction cycle from a numerical value that is obtained by dividing a radiated charge amount in the same extraction cycle by an accumulated charge amount.

(8) In the above-described item (1), said control unit preferably corrects the charged particle beam irradiation position in the next extraction cycle by a function in which a position to which the charged particle beam irradiation position changes according to the phase in the extraction cycle is approximated by a phase function of the extraction cycle.

(9) In the above-described item (1), preferably, said charged particle irradiation system is equipped with two of the charged-particle-beam-position monitor systems, with one disposed upstream of the charged-particle-beam scanning equipment and the other disposed downstream of the charged-particle-beam scanning equipment.

(10) In the above-described item (1), preferably, said charged particle irradiation system is equipped with two of the charged-particle-beam-position monitor systems, with both of them disposed downstream of the charged-particle-beam scanning equipment.

(11) In the above-described item (1), preferably, said charged particle irradiation system is equipped with one charged-particle-beam-position monitor system capable of measuring the position and the angle of the charged particle beam.

(12) In the above-described item (1), preferably, if the difference between the charged particle beam position and the desired irradiation position at the target position exceeds a threshold value, a safety interlock system is operated, said charged particle beam position having been calculated by the control unit.

(13) In the above-described item (1), preferably, said charged particle irradiation system is equipped with two of the charged-particle-beam-position monitor systems, with both of them disposed upstream of the charged-particle-beam scanning equipment.

According to the present invention, it is possible to improve irradiation positional accuracy of a charged particle beam and thereby to decrease the possibility that a normal tissue will be irradiated with it.

DETAILED DESCRIPTION OF THE PREFERRED EMBODIMENTS

The configuration of a charged particle irradiation system and the operation thereof according to one embodiment of the present invention will be described with reference to FIGS. 1 through 7.

First of all, the overall configuration of the charged particle irradiation system according to this embodiment will be described with reference to FIG. 1.

Figure 1:
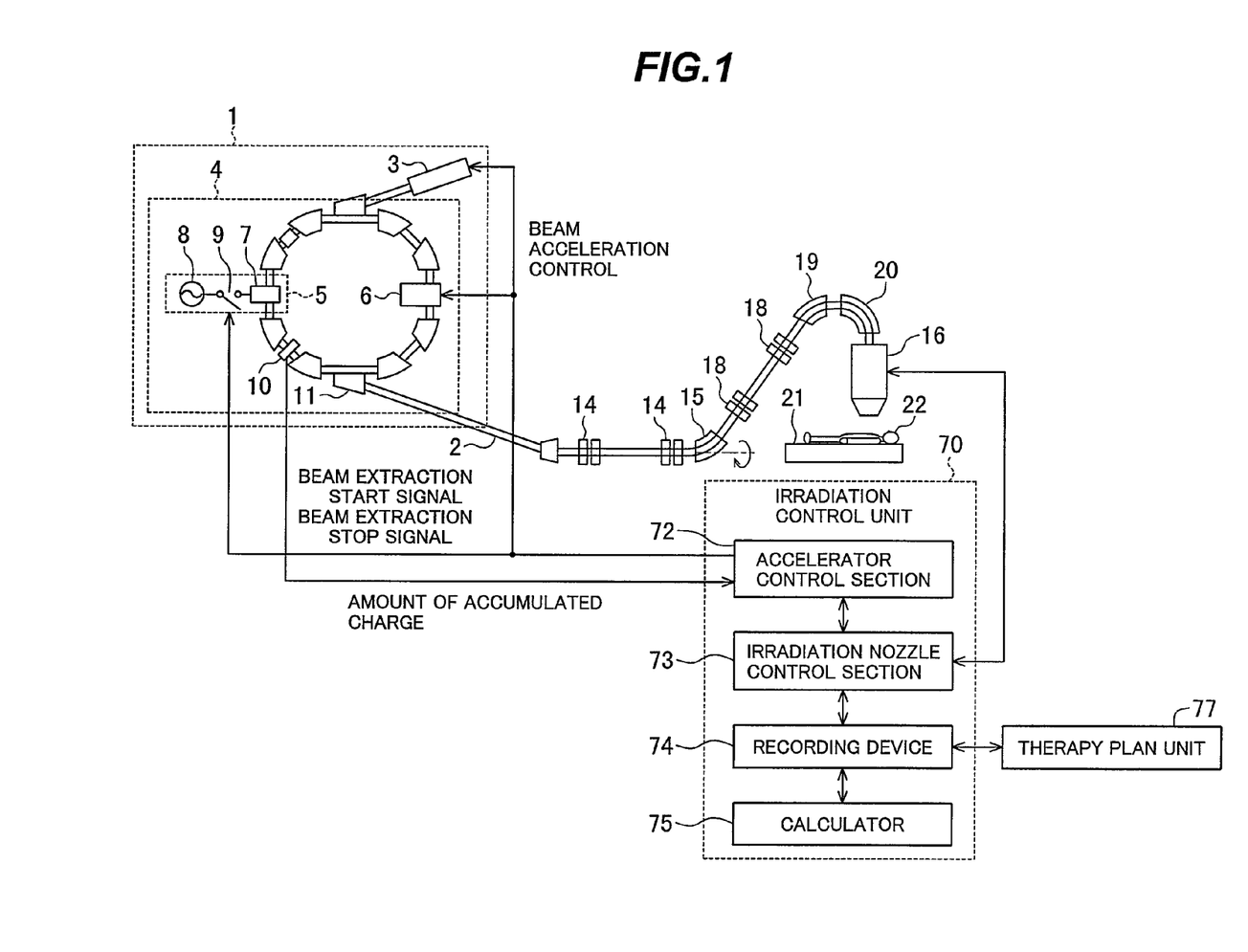
FIG. 1 is a system block diagram illustrating the overall configuration of a charged particle irradiation system according to one embodiment of the present invention.

FIG. 1 is a system block diagram illustrating the overall configuration of a charged particle irradiation system according to one embodiment of the present invention.

The charged particle irradiation system according to this embodiment includes an ion beam generator 1, a beam transport line 2, an irradiation nozzle 16, and a control unit 70.

The ion beam generator 1 includes an ion source (not illustrated), a linear accelerator 3 (preaccelerator), and a synchrotron 4. The synchrotron 4 includes a radiofrequency acceleration system 5, an acceleration system 6, and an accelerated-charge amount monitor 10. The radiofrequency acceleration system 5 includes: an radiofrequency extraction electrode 7 that is located in the closed orbit of the synchrotron 4; and a radiofrequency power supply 8. The radiofrequency extraction electrode 7 is connected to the radiofrequency power supply 8 through a switch 9. The acceleration system 6 includes: a radiofrequency acceleration cavity (not illustrated) that is located in the closed orbit; and a radiofrequency power supply (not illustrated) for applying high-frequency power to the radiofrequency acceleration cavity. Ions such as a protons and carbon are generated in the ion source. The ions are then injected into the linear accelerator 3 where they are accelerated. The ion beam extracted from the linear accelerator 3 is injected into the synchrotron 4. In the synchrotron 4, the ion beam is energized and accelerated by the high-frequency power that is applied from the radiofrequency power supply through the radiofrequency acceleration cavity to the ion beam. After the ion beam is accelerated to a predetermined energy level, a high frequency wave is applied to the ion beam by the radiofrequency acceleration system 5. The ion beam, which has been orbiting in the synchrotron 4 within its stability limit, makes a transition out of the stability limit and is extracted from the synchrotron 4 through the extraction deflector 11. The ion beam extraction stops when the application of the high-frequency wave is stopped.

In addition, the accumulated-charge amount monitor 10 is located in the closed orbit of the synchrotron 4. By measuring the amount of electric current of the ion beam, the amount C of the ion beam accumulated in the synchrotron 4 is measured.

The ion beam which has been extracted from the synchrotron 4 is transported to the irradiation nozzle 16 through the beam transport line 2. The beam transport line 2 is constituted of quadrupole magnets 14, and 18 and bending magnets 15, 19, and 20.

A rotating gantry (not illustrated) is provided with part of the beam transport line 2 and with the irradiation nozzle 16. The reverse U-shaped part of the beam transport line 2 and the irradiation nozzle 16 are placed on the generally cylinder-shaped rotating drum of the rotating gantry (not illustrated), and they can be rotated by a motor. Irradiated with the ion beam that has passed through the irradiation nozzle 16 is a target 23 of an irradiation object 22 on an irradiation bed 21 placed in the rotating cylinder of the gantry. When a tumor is irradiated, for example, the target 23 is an irradiation target that is to be irradiated with the ion beam and includes that affected part. The target 23 is somewhat larger than the affected part. In addition, the irradiation object is a human body.

The control unit 70 includes an accelerator control section 72, an irradiation nozzle control section 73, a recording device 74, and a calculator 75. The operation of the control unit 70 will be described later.

The configuration of the irradiation nozzle 16 of the charged particle irradiation system according to this embodiment is now described with reference to FIG. 2.

Figure 2:
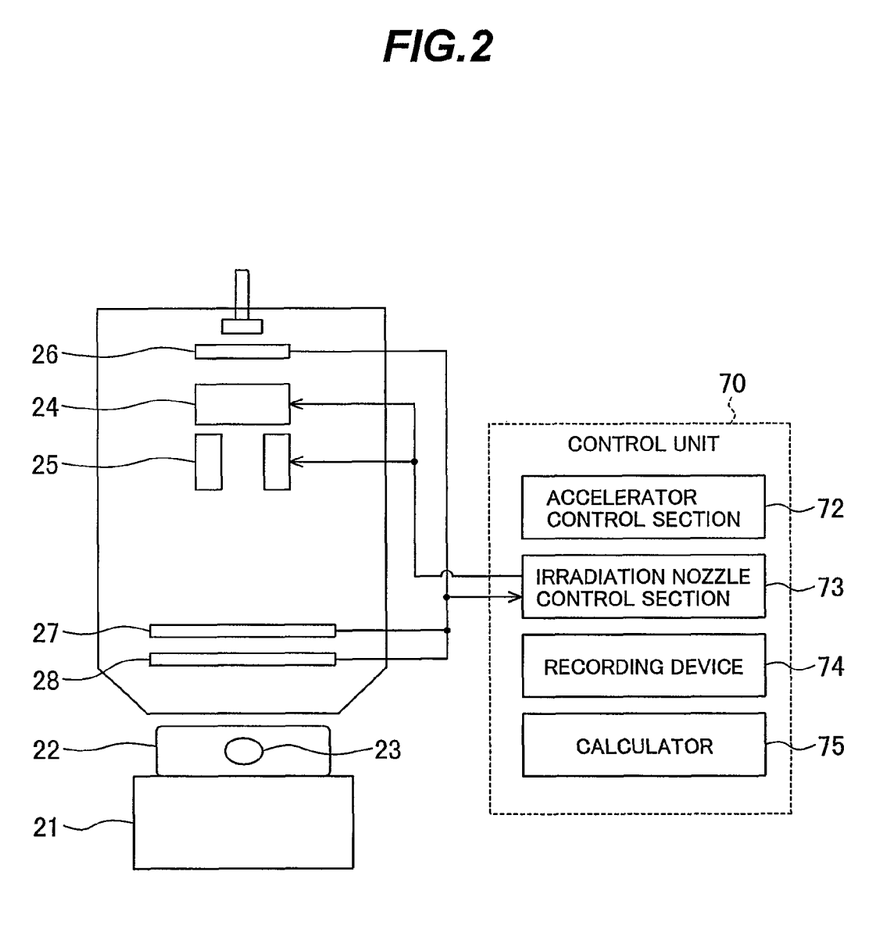
FIG. 2 is a system block diagram illustrating the configuration of an irradiation nozzle of a charged particle irradiation system according to one embodiment of the present invention.

FIG. 2 is a system block diagram illustrating the configuration of the irradiation nozzle of a charged particle irradiation system according to one embodiment of the present invention.

The irradiation nozzle 16 includes scanning magnets 24 and 25, an upstream beam position monitor 26, a downstream beam position monitor 27, and a dose monitor 28. In a plane that is vertical to the beam traveling direction, the two scanning magnets 24 and 25 deflect the beam in two directions (X and Y directions) that are orthogonal to each other so that the irradiation position is changed. The beam position monitors 26 and 27 measure the position and the spread of the ion beam. The dose monitor 28 measures the dose of the ion beam. The upstream beam position monitor 26 is located upstream of the scanning magnets, whereas the downstream beam position monitor 27 is located downstream of the scanning magnets.

Two electrodes of the dose monitor 28 form a parallel plate-type structure. Voltage is applied between the two electrodes. When the ion beam passes through the dose monitor 28, the ion beam ionizes the air in the detector. An electric field in the detector causes the ionized particles to accumulate around the electrodes. The accumulated charged particles are detected in the form of a signal. Because the amount of the ion beam is proportional to that of electric charges accumulated around the electrodes, the amount of ion beam which has passed can be measured.

The upstream beam position monitor 26 and the downstream beam position monitor 27 are provided with wires disposed in parallel at constant intervals in the X and Y directions, respectively. A high voltage is applied to the wires. When an ion beam passes, the air in the detector is ionized. As a result, the ionized particles are collected around the nearest wire. Then, a signal electric charge which is proportional to the ion beam passing through an area in proximity to the wire is accumulated in a capacitor. A voltage corresponding to the accumulated electric charge is read out from each channel. Since the distribution of the beam can be acquired by the wires disposed at intervals that are sufficiently smaller than the spread of the ion beam, the beam position (the center of gravity of the distribution) and the beam width (the standard deviation of the distribution) can be calculated.

Here, the relationship between the depth of a target and the energy of an ion beam in the charged particle irradiation system according to this embodiment is described with reference to FIG. 3.

Figure 3:
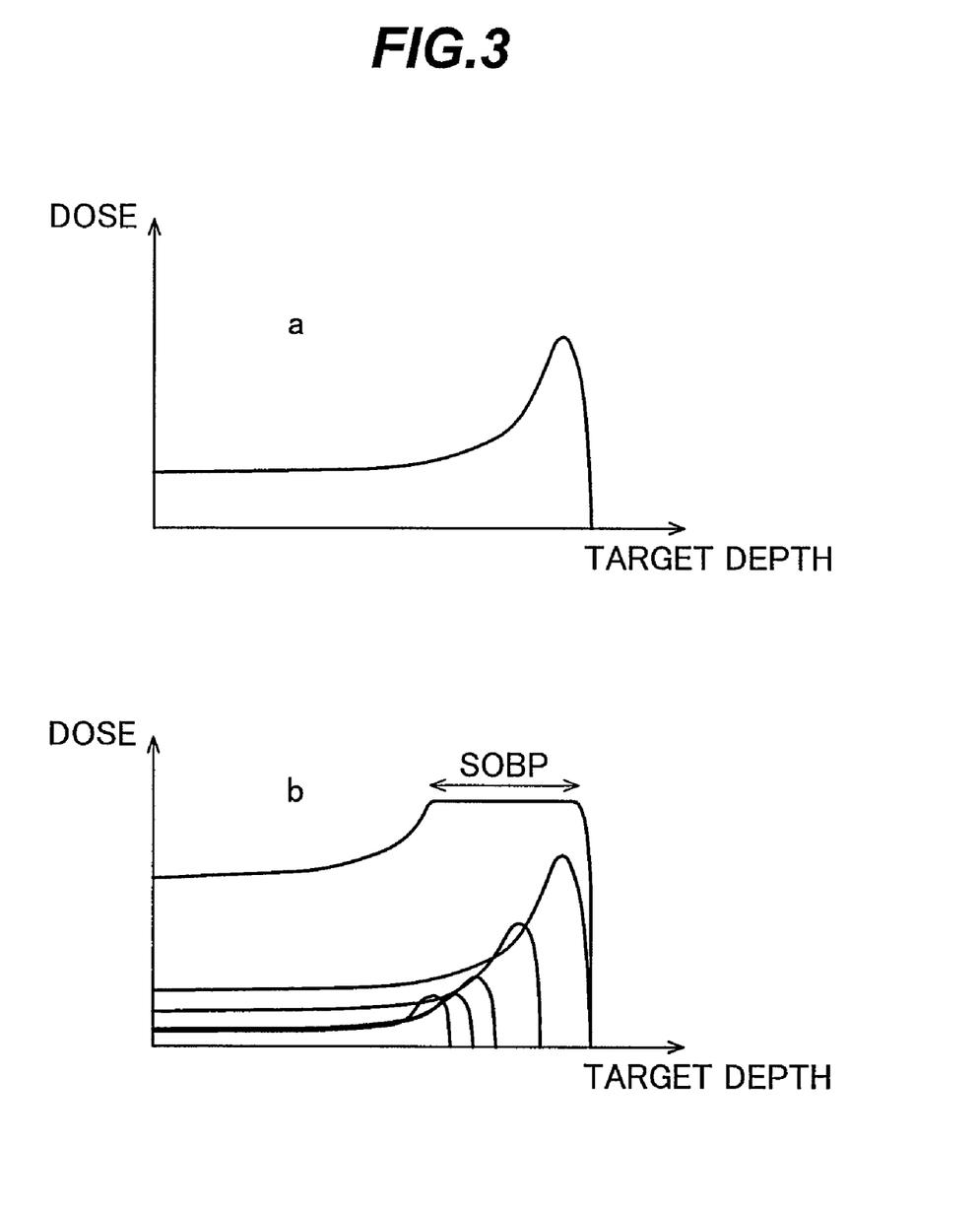
FIG. 3 is a diagram illustrating the relationship between the depth of a target and the energy of an ion beam in a charged particle irradiation system according to one embodiment of the present invention.

FIG. 3 is a diagram illustrating the relationship between the depth of a target and the energy of an ion beam in a charged particle irradiation system according to one embodiment of the present invention.

The target 23 is located inside the irradiation object 22. FIG. 3A is a graph illustrating, as a function of the depth, a dose distribution of the monoenergetic ion beam in the irradiation object 22. The peak shown in FIG. 3A is designated as a bragg peak. Because the position of the bragg peak depends on energy, adjusting the energy of the ion beam to the depth of the target 23 enables irradiation of the target 23 at the position of the bragg peak. Although the target 23 has a certain thickness in the depth direction, the bragg peak is sharp. Therefore, as shown in FIG. 3B, by irradiating with several ion beams with different energy at proper strength ratios to superimpose their bragg peaks, a uniform high dose region (SOBP) having the same thickness in the depth direction as that of the target 23 is formed.

Hereinafter, a direction that is vertical to the direction in which an ion beam is injected is referred to as a "lateral direction." The relationship between the spread of the target 23 in the lateral direction and an ion beam is now described below. After the ion beam reaches the irradiation nozzle 16, it is scanned by the two scanning magnets 24 and 25 that are disposed vertically to each other. As a result, the ion beam reaches a desired position in the lateral direction. The spread of the ion beam in the lateral direction can be approximated by Gaussian distributions. By disposing the Gaussian distributions at regular intervals each of which is approximately the standard deviation of the Gaussian distribution, the superimposed distribution has a uniform area. The irradiation with an ion beam at regular intervals in this manner by scanning the ion beam makes it possible to form a dose region uniform in the lateral direction.

As described above, the scanning magnets 24 and 25 scan an ion beam in the X and Y directions, and the energy of the ion beam is altered so as to move its bragg peak in the depth direction, which thus enables uniform irradiation of the whole target 23. Incidentally, a unit of irradiation field which is irradiated with the same energy and has its spread in the lateral direction as a result of ion-beam scanning by the scanning magnets is called a layer.

Next, the control operation of the control unit 70 will be described.

An ion beam is supplied to the synchrotron 4 from the linear accelerator 3. The synchrotron 4 accelerates the ion beam up to a set energy level. In this case, when the acceleration ends, the accelerated-charge amount monitor 10 measures the amount C of the ion beam that has been accumulated in the synchrotron 4. After that, when the irradiation of the target 23 with the ion beam accelerated to that energy level ends (in other words, the irradiation of one layer ends), the ion beam is decelerated. A new ion beam is then supplied from the linear accelerator 3 to the synchrotron 4 and accelerated to the next different energy level that has been set in order to perform further irradiation. In addition, if the irradiation of the target 23 does not end with one ion beam accelerated to a certain energy level before the ion beam which orbits in the synchrotron 4 becomes exhausted (in other words, the irradiation of one layer does not end), a new ion beam is supplied from the linear accelerator 3 to the synchrotron 4 and accelerated to the same energy level to continue the irradiation. A period during which the synchrotron 4 accelerates an ion beam supplied from the linear accelerator 3 and irradiation is completed with the one ion beam accelerated to a certain energy level or a period during which the ion beam in the synchrotron 4 is exhausted by the irradiation and another ion beam is newly supplied from the linear accelerator 3 is called an extraction cycle.

The control of irradiation in one extraction cycle will be described. The control unit 70 stops the extraction of an ion beam from the synchrotron 4 and in that state sets an excitation current value for each of the scanning magnets 24 and 25 so that the irradiation position of the ion beam is changed. After the irradiation position is changed, the control unit 70 starts the extraction of the ion beam. After the dose of the ion beam reaches a set value, the control unit 70 stops the extraction of the ion beam again and sets an excitation current value for each of the scanning magnets 24 and 25 so that the irradiation position of the ion beam is changed. During the extraction of the ion beam, the control unit 70 keeps constant the excitation current values of the scanning magnets 24 and 25. This one irradiation is called a spot. The irradiation of the target 23 starts by starting the extraction from the synchrotron 4 whereas the irradiation stops by stopping the extraction.

A list which associates irradiation positions with the amounts of excitation current is provided beforehand as a table. This table is configured such that if the position and the angle of an ion beam received from the ion beam generator 1 do not change at all, an irradiation position coincides with a target irradiation position. Here, target irradiation position means desired irradiation position. Hereinafter, the position and angle of the ion beam are designated as "base conditions." The incident angle of an ion beam incident on the irradiation nozzle under the base conditions is vertical to each device included in the irradiation nozzle 16.

The recording device 74 records irradiation information. The irradiation information includes: irradiation angles on a spot basis (more specifically, the rotation angle of the gantry); irradiation positions (hereinafter referred to as "target irradiation positions"); energy; and radiation doses. Before irradiation, irradiation planning equipment 77 is used to determine in advance a target 23 on the basis of an image taken by CT or the like. Irradiation information is created from the target 23, and the created irradiation information is recorded in the recording device 74.

The accelerator control section 72 controls the ion beam generator 1, the beam transport line 2, and the rotating gantry to accelerate, extract, or stop an ion beam. The accelerator control section 72 receives the irradiation information from the recording device 74 and then rotates the rotating gantry to the irradiation angle included in the irradiation information to accelerate the ion beam up to the energy level included in the irradiation information. Moreover, the accelerator control section 72 controls each magnet included in the beam transport line 2 and sets an excitation current values for each of the magnets so that the accelerated ion beam reaches the irradiation nozzle 16. The accelerator control section 72 controls the radiofrequency acceleration system 6 by use of an extraction permission signal received from the irradiation nozzle control section 73 to apply a high frequency wave to an ion beam and extracts the ion beam. In addition, the accelerator control section 72 controls the radiofrequency acceleration system 6 by use of a beam stop signal received from the irradiation nozzle control section 73, thereby stopping the application of the high frequency and the extraction of the ion beam. Moreover, the accelerator control section 72 receives information about the amount C of the ion beam from the accelerated-charge amount monitor 10.

The irradiation nozzle control section 73 sets the amount of excitation current to be fed to the scanning magnets 24 and 25 and reads out signals from the dose monitor 28 and the beam position monitors 26 and 27. The irradiation nozzle control section 73 receives from the calculator 75 an excitation current value that has been calculated by the calculator 75 on the basis of the irradiation information recorded in the recording device 74. After the accelerator control section 72 accelerates an ion beam up to the energy level specified by the irradiation information, the irradiation nozzle control section 73 sets an excitation current value for each of the scanning magnets 24 and 25 which is specified by the calculator 75 and then transmits an extraction permission signal to the accelerator control section 72. Then, an ion beam is extracted; the dose of the ion beam with which the target 23 has been irradiated is detected as a signal of the dose monitor 28. The irradiation nozzle control section 73 includes a current-to-pulse converter (not illustrated) and a dose counter (not illustrated). A signal of the dose monitor 28 is quantized by the current-to-pulse converter and is counted by the dose counter. The value of the dose counter corresponding to the dose specified by the irradiation information is calculated and set beforehand as a counter target value. When a value of the counter coincides with the counter target value, the irradiation nozzle control section 73 transmits an extraction stop signal to the accelerator control section 72. Moreover, the irradiation nozzle control section 73 reads out signals from the beam position monitors 26 and 27 and calculates the position and width of an ion beam on the basis of the signals.

There is a possibility that the actual position and angle of an ion beam extracted from the ion beam generator 1 will be unstable. If the state of the ion beam which has been injected into the irradiation nozzle 16 differs from the base conditions, the use of excitation current values listed in the table causes an irradiation position to be away from a target irradiation position. Therefore, in order to reduce fluctuations from the target irradiation position, the calculator 75 corrects the value of the excitation current set to the scanning magnet with the use of a value listed in the table on the basis of information obtained in the immediately preceding extraction cycle. According to this embodiment, when the irradiation in one extraction cycle is completed, the calculator 75 receives the position and the dose of an ion beam of each spot in an extraction cycle, which have been calculated by the irradiation nozzle control section 73. The calculator 75 then calculates a set value of the excitation current to be fed to each of the scanning magnets 24 and 25 for each spot in the immediately ensuing extraction cycle.

The reason the correction is made on the basis of information on the immediately preceding extraction cycle is given below. During irradiation, the same layer is rarely irradiated in two extraction cycles or more; in many cases, a different-depth layer is irradiated in each extraction cycle. To be more specific, the target 23 is irradiated with an ion beam having a different energy level in each extraction cycle. If the energy level is the same, the fluctuations of an ion beam from the base conditions are the same in each extraction cycle. However, if the energy level is different, the fluctuations of a beam position and a beam angle from the base conditions differ; in that case, it is difficult to make correction. However, by irradiating layers starting from a deep layer towards a shallower layer in succession or by irradiating layers starting from a shallow layer towards a deeper layer in succession so as to successively irradiate layers that are adjacent to each other, the fluctuation differences due to different energy levels are slight even if the energy level is changed. If the difference in energy is small, changes in position and angle of an ion beam from the base conditions are similar. As a result, the correction becomes effective.

In addition to the ion beams which change from the base conditions on an extraction cycle basis, there are ion beams which change over a longer period of time than that of an extraction cycle regardless of extraction cycles. Moreover, the position and the angle of an ion beam may differ on a daily basis due to the temporal changes of various devices. Also in such cases, it is possible to increase the accuracy in irradiation position by use of a correction method based on beam information about the immediately preceding extraction cycle according to this embodiment.

The correction method according to this embodiment will be described below.

The first step of the correction is to calculate the difference between an irradiation position and a target irradiation position at a target position of each spot in the immediately preceding extraction cycle, which target position is calculated from beam positional information of the upstream beam position monitor 26 and the downstream beam position monitor 27. In order to correctly make a correction, it is necessary to determine the correction amount on the basis of the difference between the irradiation position and the target irradiation position and information on the target irradiation position. However, because fluctuations of an ion beam angle from the base conditions caused by the accelerator is very small, adoption of the following correction method enables increase in irradiation positional accuracy, in which only the difference between the irradiation position and the target position is used irrespective of the target irradiation position.

An X-directional correction process performed by the charged particle irradiation system according to this embodiment will be described with reference to FIGS. 4 through 6.

Figure 4:
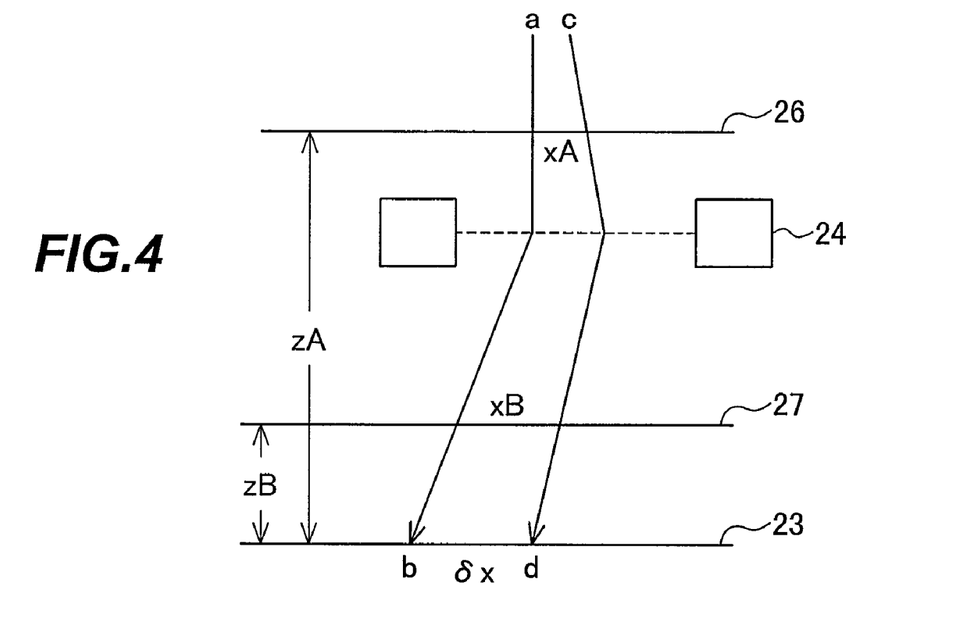
FIG. 4 is a diagram illustrating beam behavior inside the irradiation nozzle of a charged particle irradiation system according to one embodiment of the present invention.
Figure 5:
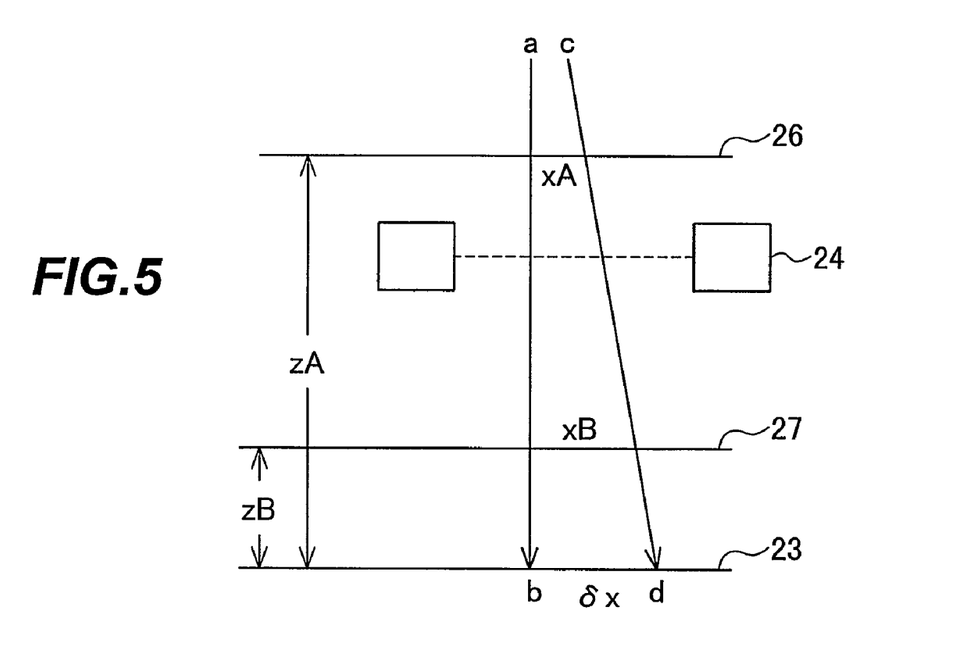
FIG. 5 is a diagram illustrating beam behavior inside the irradiation nozzle of a charged particle irradiation system according to one embodiment of the present invention.
Figure 6:
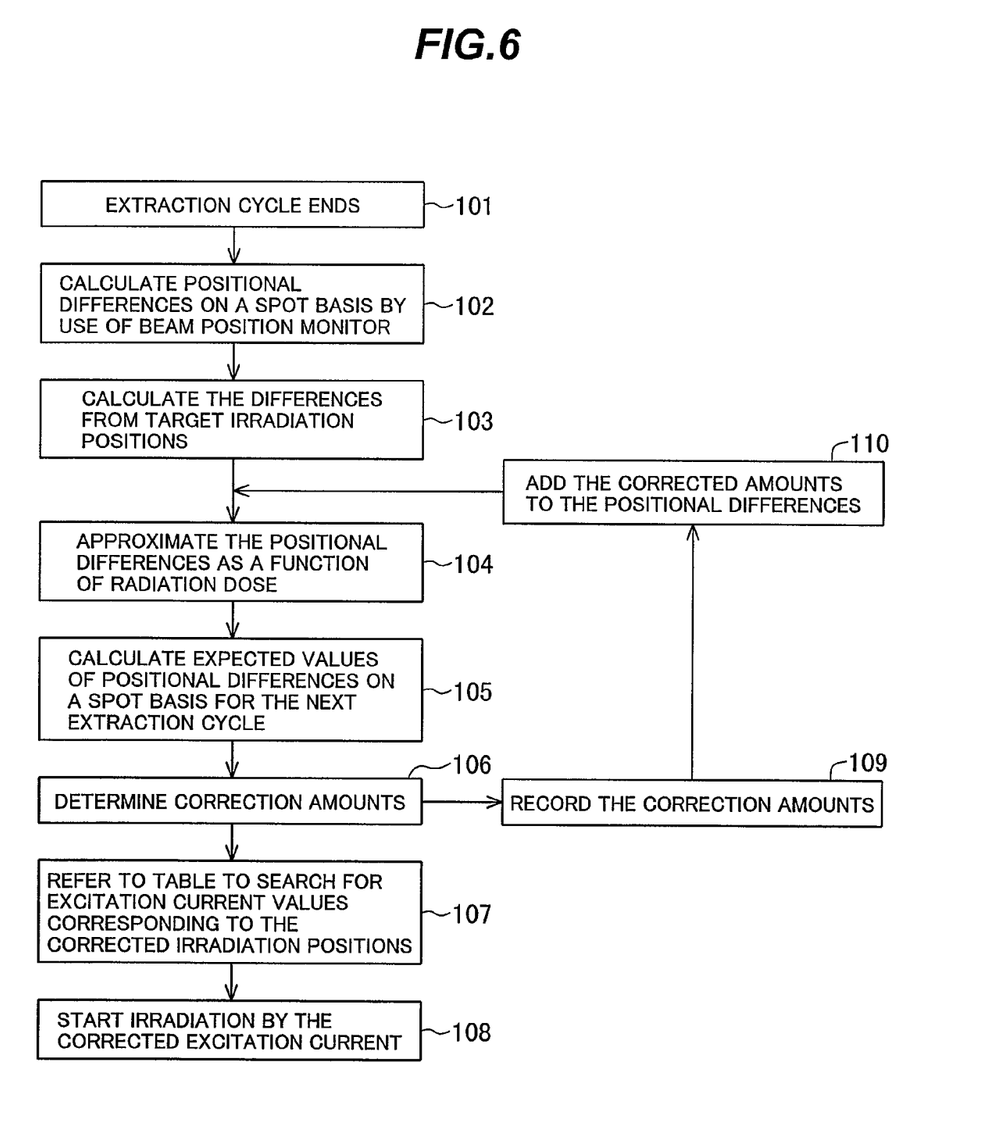
FIG. 6 is a flowchart illustrating a correction method used in the control unit of a charged particle irradiation system according to one embodiment of the present invention.

FIGS. 4 and 5 are diagrams each illustrating beam behavior inside the irradiation nozzle of a charged particle irradiation system according to one embodiment of the present invention. FIG. 6 is a flowchart illustrating a correction method used in the control unit of a charged particle irradiation system according to one embodiment of the present invention.

In FIG. 4, an ion beam, which is kept in the base conditions, is injected into the irradiation nozzle 16 from position a. The ion beam is then scanned by the scanning magnet 24. As a result, the ion beam reaches a target irradiation position b. On the other hand, if the correction is not performed, an ion beam injected from a position c, which is not kept in the base conditions, is scanned by the scanning magnet 24 that is set at the same excitation current value. As a result, the ion beam reaches a position d. Here, in comparison with the change in ion beam position from the base conditions in the scanning magnet which change is caused by the ion beam generator 1, the difference in deflection angle caused by the scanning magnet is slight. To be more specific, an ion beam injected from position a and an ion beam injected from the position c are deflected by the same angle. Because this deflection angle is about 0.1 rad at the maximum, the system shown in FIG. 4 approximates to the system shown in FIG. 5. As shown in FIGS. 4 and 5, the differences between the path (reference path) from position a to the position b and the path from the position c to the position d at the positions of the beam position monitors 26 and 27 are expressed as xA and xB, respectively.

Next, the correction method used by the control unit of the charged particle irradiation system according to this embodiment will be described with reference to FIG. 6.

In step 101, an extraction cycle ends by the accelerator control section 72. After that, in step 102, the irradiation control unit 73 calculates the difference xA and xB.

Next in step 103, the calculator 75 calculates the difference $\delta x = xA + (xB - xA) \times zA/(zA - zB)$ where the distance from the upstream beam position monitor 26 to the target position is zA, and the distance from the downstream beam position monitor 27 to the target 23 is zB. This difference $\delta x$ is the difference between a target irradiation position and an actual irradiation position at the target position. For all spots in one extraction cycle, the difference $\delta x$ is calculated.

Next in step 104, the calculator 75 uses information about the quantity of the electric charge radiated during each spot to approximate the relationship between a radiated charge amount D during an extraction cycle (more specifically, the total dose of spots up to the immediately preceding spot in the same cycle, which is converted into the quantity of electric charge) and the difference $\delta x$ by a proper function, for example, a cubic function ($\delta x = f(D)$).

Next in step 105, for a radiated charge amount D' of each spot during the next extraction cycle (the total dose of spots up to the immediately preceding spot in the same extraction cycle, which is converted into the quantity of electric charge), the calculator 75 calculates from the function obtained by the approximation the estimated value $\delta x'$ of each positional difference in each spot in the next extraction cycle by use of the equation of $\delta x' = f(D')$.

In step 106, the calculator 75 determines a correction amount ($\Delta x' = \delta x'$). In step 107, at the target irradiation position x0', the calculator 75 refers to the table to search for the excitation current value corresponding to $x0' + \Delta x'$ and then transmits the excitation current value to the irradiation nozzle control section.

Lastly in step 108, the irradiation control unit 73 starts the irradiation.

The above-described calculation is also performed for the Y direction in the same manner.

Here, if the last extraction cycle to be corrected has also been corrected, the correction amount $\Delta x$ in that cycle is recorded in the calculator 75 in step 109. In step 110, $\delta x$ is replaced with $\delta x + \Delta x$, and then calculation is performed by the above-described steps.

According to this correction method, after the irradiation starts, the correction cannot be performed in the first extraction cycle: it is performed for spots in the second extraction cycle or later. Therefore, test irradiation may be performed before the irradiation so that an approximate curve ($\delta x = f(D)$) is acquired beforehand. In addition, the correction amount $\Delta x'$ may also be determined beforehand for the first extraction cycle.

Next, correction effects on an irradiation position at a target position by the charged particle irradiation system according to this embodiment will be described with reference to FIG. 7.

Figure 7:
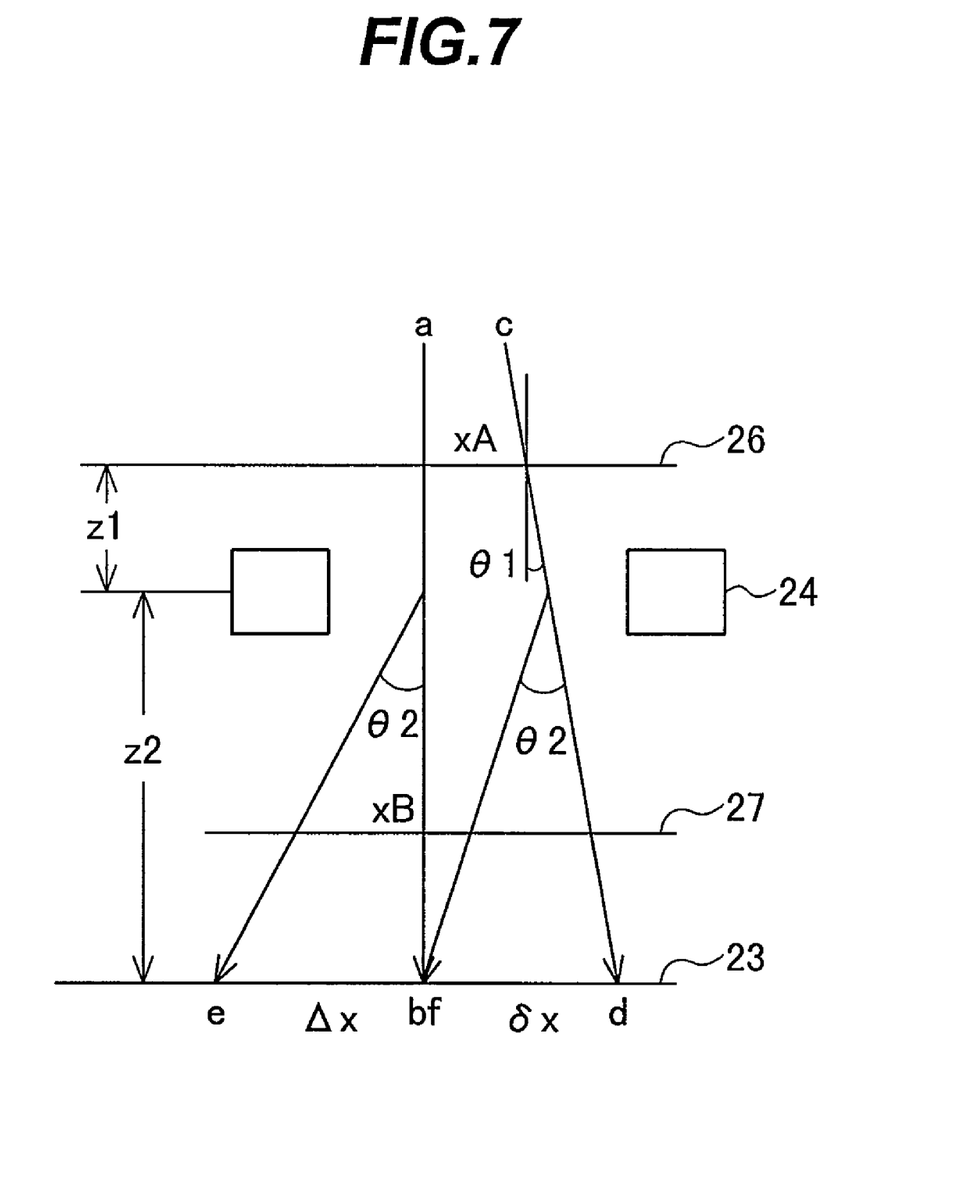
FIG. 7 is a diagram illustrating correction effects on an irradiation position at a target position by a charged particle irradiation system according to one embodiment of the present invention.

FIG. 7 is a diagram illustrating correction effects on an irradiation position at a target position by a charged particle irradiation system according to one embodiment of the present invention.

As is the case with FIG. 5, FIG. 7 illustrates the inside of an irradiation nozzle. It is assumed that the distance from the upstream beam position monitor 26 to the scanning magnet 24 is z1 and that the distance from the scanning magnet 24 to the target 23 is z2. Here, an ion beam kept in the base conditions travels from position a to position b. On the other hand, an ion beam whose position and angle have changed from the base conditions travels from position c to position d. $\delta x$ is determined by the calculation in step 103. It is assumed that an angle which an ion beam injected into the irradiation nozzle 16 forms with the base conditions is $\theta 1$ and that an angle obtained by the correction is $\theta 2$. To be more specific, $\Delta x = \delta x$; an excitation current value to be set to the scanning magnet is the same as the value at which an ion beam in the base conditions travels toward position e. Accordingly, the equations of $\theta 1 = (\delta x - xA)/(z1 + z2)$ and $\theta 2 = \delta x/z2$ hold. The correction by the scanning magnet causes the beam irradiation position of the ion beam injected from position c to move to position f. When the difference between positions e and f is calculated, the value of e agrees with that of f because $xA + \theta 1 \times z1 - (\theta 2 - \theta 1) \times z2 = 0$. Therefore, it is understood that the correction is right. The above-described calculation can also be applied to the Y direction in the same manner.

In the above-described correction, the radiated charge amount D is used to identify the phase of an extraction cycle (spot position in the extraction cycle). However, by identifying the phase progress of an extraction cycle by D/C where c is the accumulated charge amount in an extraction cycle ($\delta x = f(D/C)$), it is possible to more correctly perform the correction. This method is effective particularly when the accumulated charge amount largely changes on an extraction cycle basis.

The upstream beam position monitor may also be located on the downstream side of the scanning magnet. As is the case with the above-described embodiment, by defining the distances from the base conditions at the positions of the two beam position monitors as xA and xB, respectively, the same calculations apply. If the two beam position monitors are located downstream of the scanning magnet, position monitoring accuracy improves.

In contrast, both of the two beam position monitors may also be located on the upstream side of the scanning magnet. According to the above-described embodiment, it is also possible to perform the correction by determining the position and the angle of an ion beam in the irradiation nozzle from beam position information acquired by the two position monitors located in the beam transport line 2.

The above description as to the correction is based on the assumption that correction is made on a synchrotron cycle basis. However, it is also possible to make a correction on a specified cycle basis. To be more specific, for example, it is also possible to make a correction every two synchrotron cycles. In addition, it is also possible to correct the next spot position by use of positional information of the last spot. Moreover, it is also possible to correct the positions of successive beams on a certain cycle basis.

It is also possible to use such a beam position monitor that is capable of monitoring both a position and an angle by itself. Methods for measuring both the position and angle include a method in which a scintillation beam from a scintillator or a scintillation fiber is measured by use of a photoelectron multiplier or a CCD camera or a method in which it is measured by providing wires in multiple layers.

It is at the end of an extraction cycle that the calculator 75 according to this embodiment acquires information about the beam position monitored by the beam position monitor from the irradiation nozzle control section. Here, it is possible to determine an irradiation position at a target position every time a spot ends by receiving beam position information from the irradiation nozzle control section every time a spot ends.

In order to prevent positions outside the target 23 from being irradiated, it is necessary to stop the irradiation by operating a safety interlock system when an irradiation position is largely apart from a target irradiation position. Heretofore, in order to prevent irradiation of non-target irradiation positions, a safety interlock system is operated when a beam position at the position of a beam position monitor exceeds a threshold value on a spot basis. However, if the position at the position of the beam position monitor is away from a specified position by more than a threshold value, and further if an irradiation position agrees with a target irradiation position on the target 23, the safety interlock system operates even if the operation of the safety interlock system is not required. This lowers efficiency in the use of the irradiation system.

An irradiation position is calculated at a target position on a spot basis, a threshold value for the distance from a target irradiation position to the irradiation position is set, and the safety interlock system is adapted to operate when the threshold value is exceeded. This allows the tolerance of the monitor to be moderated, with the result that the number of times the safety interlock system is operated is reduced to the required minimum. Therefore, it is possible to increase irradiation efficiency.

As described above, according to this embodiment, it is possible to improve irradiation positional accuracy of a charged particle beam and thereby to decrease the possibility that a normal tissue will be irradiated with the charged particle beam.

Moreover, because it is possible to moderate requirements for the accuracy in position and angle of an ion beam, which are required by the ion beam generator, it is possible to shorten the adjustment period of the accelerator. This makes it possible to reduce costs.

Furthermore, by increasing irradiation positional accuracy, it is possible to reduce the number of times the safety interlock system of the irradiation nozzle is operated. The reduction in the number of times the safety interlock system is operated makes it possible to shorten the average time taken per irradiation. Therefore, it is possible to increase the number of times irradiation is performed within a specified period of time.

What is claimed is:

1. A charged particle irradiation system comprising:
    an accelerator for extracting a charged particle beam;
    charged-particle-beam scanning equipment; and
    a charged-particle-beam-position monitor system,
    wherein said charged particle irradiation system further includes a control unit for calculating a beam position at a target position on the basis of a signal received from the charged-particle-beam-position monitor system to control the charged-particle-beam scanning equipment so that the charged particle beam is moved to a desired irradiation position at the target position, and
    wherein in each predetermined cycle of the accelerator, said control unit corrects the value of an excitation current applied to the charged-particle-beam scanning equipment on a specified cycle basis on the basis of information about the position and the angle of the charged particle beam.

2. The charged particle irradiation system according to claim 1, wherein:
    said charged particle irradiation system is equipped with two of the charged-particle-beam-position monitor systems; and
    wherein in each predetermined cycle of the accelerator, said control unit corrects the value of the excitation current applied to the charged-particle-beam scanning equipment on a specified cycle basis on the basis of information about the position and the angle of the charged particle beam which are obtained from a first charged-particle-beam position detected by a first charged-particle-beam-position monitor system and a second charged-particle-beam position detected by a second charged-particle-beam-position monitor system.

3. The charged particle irradiation system according to claim 2, wherein:
    in each extraction cycle of the accelerator, said control unit corrects the value of an excitation current applied to the charged-particle-beam scanning equipment on the basis of information about the position and the angle of the charged particle beam.

4. The charged particle irradiation system according to claim 2, wherein:
    said control unit sets an excitation current value for the charged-particle-beam scanning equipment such that in the next cycle, a point on the opposite side of the charged particle beam position with respect to the desired irradiation position, which point is away from the beam position by the distance between the beam position and the desired position at the target position, is irradiated with such a charged particle beam with which the beam position agrees with the desired irradiation position.

5. The charged particle irradiation system according to claim 2, wherein:
    even when the charged-particle-beam scanning equipment scans the charged particle beam, said control unit calculates the distance between the desired position and the charged particle beam position at the target position on the basis of the distance between the position of the charged particle beam traveling toward the desired irradiation position at the position of the charged-particle-beam-position monitor system and the path of the charged particle beam.

6. The charged particle irradiation system according to claim 2, wherein:
said first charged-particle-beam-position monitor system is disposed upstream of the charged-particle-beam scanning equipment and said second charged-particle-beam-position monitor system is disposed downstream of the charged-particle-beam scanning equipment.

7. The charged particle irradiation system according to claim 2, wherein:
said first and second charged-particle-beam-position monitor systems are disposed downstream of the charged-particle-beam scanning equipment.

8. The charged particle irradiation system according to claim 2, wherein:
said first and second charged-particle-beam-position monitor systems are disposed upstream of the charged-particle-beam scanning equipment.

9. The charged particle irradiation system according to claim 3, wherein:
said control unit identifies the progress of the phase of the extraction cycle from a radiated charge amount in the same extraction cycle.

10. The charged particle irradiation system according to claim 3, wherein:
said control unit identifies the progress of the phase of the extraction cycle from a numerical value that is obtained by dividing a radiated charge amount in the same extraction cycle by an accumulated charge amount.

11. The charged particle irradiation system according to claim 3, wherein:
said control unit corrects the charged particle beam irradiation position in the next extraction cycle by a function in which a position to which the charged particle beam irradiation position changes according to the phase in the extraction cycle is approximated by a phase function of the extraction cycle.

12. The charged particle irradiation system according to claim 1, wherein:
said charged particle irradiation system is equipped with one charged-particle-beam-position monitor system, said monitor system being capable of measuring both the position and the angle of the charged particle beam.

13. The charged particle irradiation system according to claim 1, wherein:
if the difference between the charged particle beam position and the desired irradiation position at the target position exceeds a threshold value, a safety interlock system is operated, said charged particle beam position having been calculated by the control unit.

14. The charged particle irradiation system according to claim 12, wherein:
in each extraction cycle of the accelerator, said control unit corrects the value of an excitation current applied to the charged-particle-beam scanning equipment on the basis of information about the position and the angle of the charged particle beam.

15. The charged particle irradiation system according to claim 12, wherein:
said control unit sets an excitation current value for the charged-particle-beam scanning equipment such that in the next cycle, a point on the opposite side of the charged particle beam position with respect to the desired irradiation position, which point is away from the beam position by the distance between the beam position and the desired position at the target position, is irradiated with such a charged particle beam with which the beam position agrees with the desired irradiation position.

16. The charged particle irradiation system according to claim 12, wherein:
even when the charged-particle-beam scanning equipment scans the charged particle beam, said control unit calculates the distance between the desired position and the charged particle beam position at the target position on the basis of the distance between the position of the charged particle beam traveling toward the desired irradiation position at the position of the charged-particle-beam-position monitor system and the path of the charged particle beam.

17. The charged particle irradiation system according to claim 14, wherein:
said control unit identifies the progress of the phase of the extraction cycle from a radiated charge amount in the same extraction cycle.

18. The charged particle irradiation system according to claim 14, wherein:
said control unit identifies the progress of the phase of the extraction cycle from a numerical value that is obtained by dividing a radiated charge amount in the same extraction cycle by an accumulated charge amount.

19. The charged particle irradiation system according to claim 14, wherein:
said control unit corrects the charged particle beam irradiation position in the next extraction cycle by a function in which a position to which the charged particle beam irradiation position changes according to the phase in the extraction cycle is approximated by a phase function of the extraction cycle.

* * * * *